United States Patent [19]
Timothy et al.

[11] Patent Number: 4,919,649
[45] Date of Patent: Apr. 24, 1990

[54] FLUID DELIVERY SYSTEM

[75] Inventors: Earle J. Timothy, Clinton; Edward W. Jackson, Northford; Joseph A. Mingrone; Jeffrey W. Jolie, both of New London; Dennis L. Nudelman, Waterford; John F. Howard, Brookfield, all of Conn.

[73] Assignee: Sherwood Medical Company, St. Louis, Mo.

[21] Appl. No.: 103,437

[22] Filed: Sep. 30, 1987

[51] Int. Cl.$^5$ ............................................. A61M 5/00
[52] U.S. Cl. ........................... 604/65; 128/DIG. 13; 604/151; 604/250
[58] Field of Search ............... 128/DIG. 12, DIG. 13; 604/65, 67, 131, 151, 152, 246, 247, 249, 250, 260, 7, 403, 407–410; 417/26, 28, 36, 44; 222/14–21, 23, 63–65, 71, 309, 333

[56] References Cited

U.S. PATENT DOCUMENTS

| | | | |
|---|---|---|---|
| 2,625,933 | 1/1953 | Salisbury | 604/7 |
| 2,689,565 | 9/1954 | Gobel | 604/152 |
| 3,512,748 | 5/1970 | Wilson | 604/250 |
| 3,543,752 | 12/1970 | Hesse et al. | 604/152 |
| 3,625,211 | 12/1971 | Butler . | |
| 3,690,318 | 9/1972 | Gorsuch . | |
| 3,739,943 | 6/1973 | Wilhelmson et al. . | |
| 4,089,624 | 5/1978 | Nichols et al. | 604/152 |
| 4,121,584 | 10/1978 | Turner et al. . | |
| 4,207,871 | 6/1980 | Jenkins . | |
| 4,262,668 | 4/1981 | Schmidt . | |
| 4,319,568 | 3/1982 | Tregoning | 604/151 |
| 4,490,135 | 12/1984 | Troutner | 604/67 |
| 4,576,603 | 3/1986 | Moss | 604/246 |
| 4,608,042 | 8/1986 | Vanderveen et al. | 128/DIG. 12 |

FOREIGN PATENT DOCUMENTS 0145825  6/1985  European Pat. Off. ............ 604/131

OTHER PUBLICATIONS

Huey, Florence L., "What's on the Market? A Nurse's Guide", American Journal of Nursing/Jun. 1983, pp. 902–910.

Steel, Jennifer, "Too Fast or Too Slow—The Erratic IV", American Journal of Nursing/Jun. 1983, pp. 898–901.

Primary Examiner—Stephen C. Pellegrino
Assistant Examiner—Ralph Lewis
Attorney, Agent, or Firm—Andrew J. Beck; Montgomery W. Smith; Charles Smith

[57] ABSTRACT

A fluid delivery system is provided with a disposable delivery set which includes an inlet tube, an outlet tube and a column tube connected to a syringe. A motor set is arranged to operate the syringe while sensing the level of fluid in the column tube, whereby the syringe may be reciprocated to provide incremental volumes of fluid to a patient.

16 Claims, 8 Drawing Sheets

FIG · 1

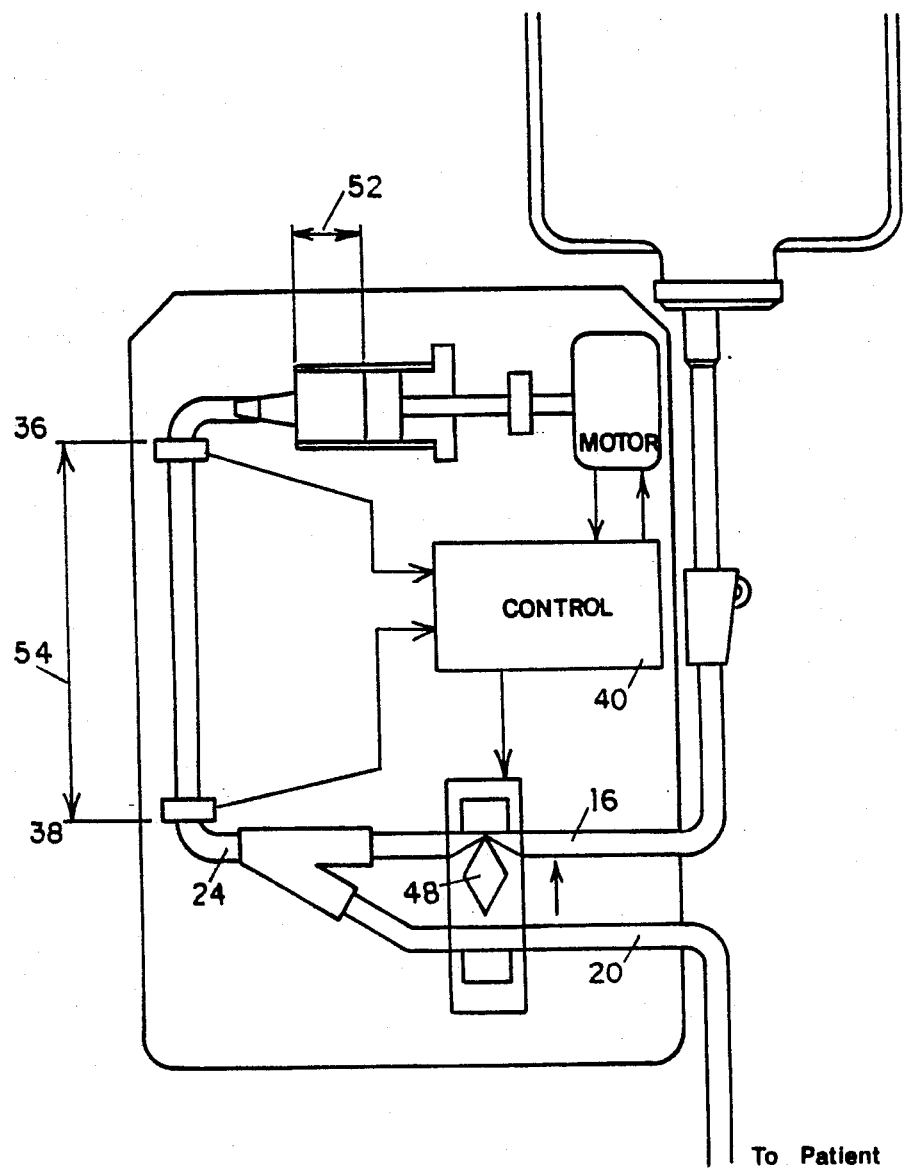
FIG · 2B

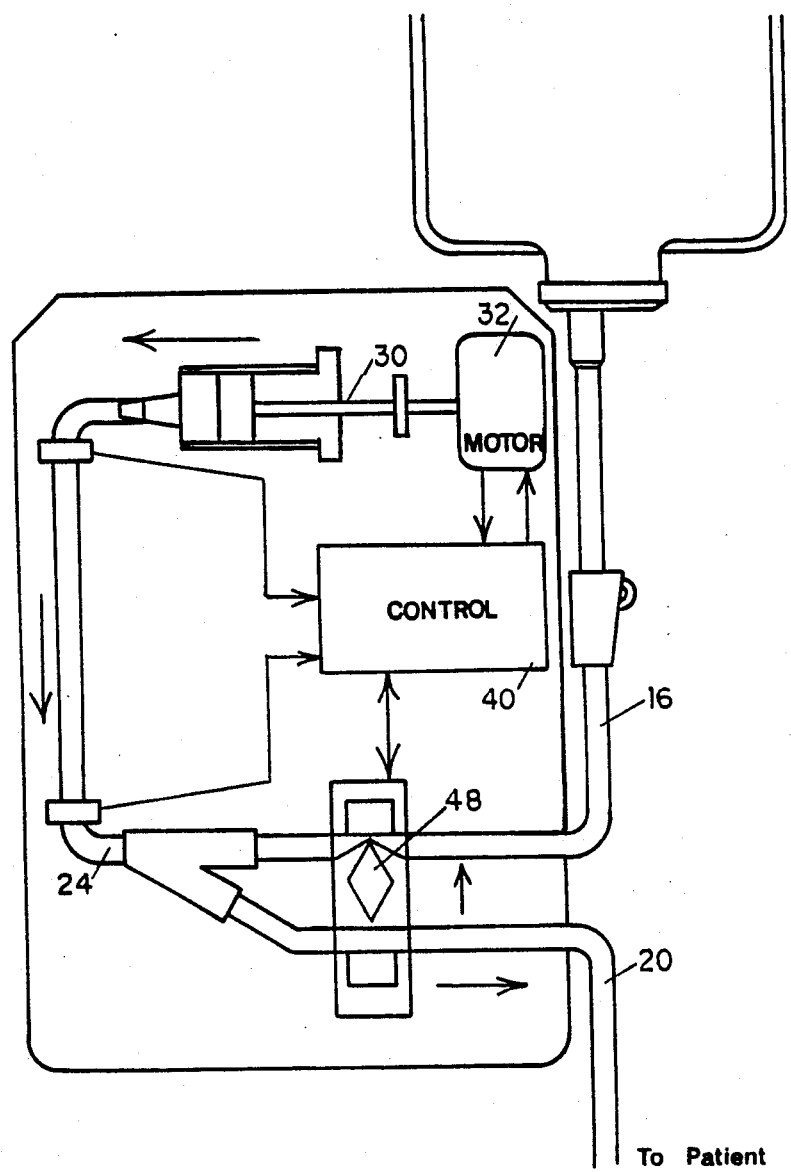
FIG · 2C

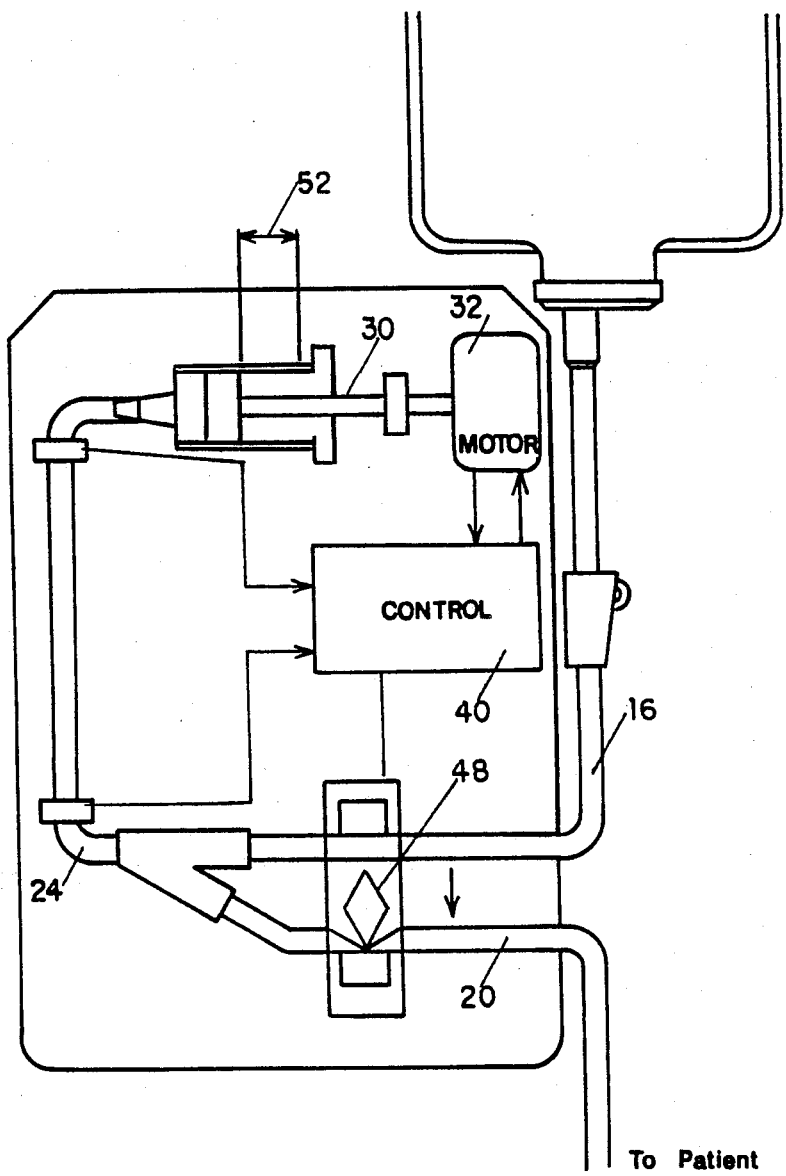
FIG·2D

FLUID DELIVERY SYSTEM

BACKGROUND OF THE INVENTION

This invention relates to fluid delivery pumping systems, and particularly to systems which are used to provide enteral or parenteral nutrition fluids to a patient.

Several pumping systems are currently in use for delivery of parenteral (intravenous) fluids to the blood vessels of a patient, delivery of enteral nutrition fluids to the stomach or intestine of a patient or delivery of blood or plasma to a patient.

Pumping systems have the advantage of delivering a measured and more accurate dose of fluids to a patient by controlling the fluid flow through the positive action of a fluid pump. Such fluid delivery systems usually involve a motor set, which provides the pumping power, and a disposable delivery set, which includes the plastic tubing which is attached to the motor set and through which either enteral or parenteral fluid is pumped into the patient. Traditionally, such sets are arranged so that the fluid is entirely contained within the set during the pumping action. Commonly used pumping actions include peristaltic pumps and diaphragm pumps wherein the pumping chamber is included as part of the disposable delivery set.

U.S. Pat. No. 3,739,943 discloses an infusion pumping system which uses a delivery set having a disposable piston type syringe and disposable valve. In the system described in this patent, intravenous fluid is directly pumped by the disposable syringe acting in connection with the valve. The volume of fluid delivered by each stroke of the syringe piston is controlled by use of magnetic limit switches. This prior art system provides effective pumping of fluid, but requires the use of a valve arrangement in a disposable pump set which renders the set relatively complex and expensive to manufacture. Further, the delivery set and syringe pump must be primed to be devoid of air prior to use and includes no inherent mechanism for detecting fluid delivery problems.

It is an object of the present invention to provide a fluid delivery set which provides accurate fluid delivery rates, when operated in connection with a pump mechanism, and which also provide a low-cost disposable pump set.

It is a further object of the invention to provide a fluid delivery system which provides detection of fluid delivery problems.

It is a further object of the invention to provide a pump unit for operation with a disposable delivery set and to provide the combination of a pump unit and a disposable set into a fluid delivery system. The present invention additionally involves a new and improved method for pumping fluids from a fluid supply to a fluid outlet in carefully controlled incremental fluid volumes.

SUMMARY OF THE INVENTION

In accordance with the present invention there is provided a delivery set for a fluid delivery system which includes a fluid inlet conduit for connection to a supply of fluid, a first compressible valve section in the fluid inlet conduit, a fluid outlet conduit and a second compressible valve section in the fluid outlet conduit. There is further included in the delivery set a fluid column having a selected length and diameter corresponding to an incremental fluid volume. A three-way junction is provided connecting the fluid inlet conduit the fluid outlet conduit and the fluid column. Means are provided for varying air pressure in the fluid column thereby to pump fluid.

In accordance with the invention there is further provided a fluid delivery system which includes a fluid delivery set and a motor set. The motor set includes first and second compressible valve operating means, first and second vertically spaced apart fluid sensing means and a reciprocating motor. Control means are provided for controlling operation of the valve operating means and the motor to open the first valve, close the second valve and operate the motor in a first direction until fluid is detected by the first sensing means and to close the first valve and to open the second valve and operate the motor in a second direction until fluid is no longer detected by the second sensing means. The disposable delivery set includes a fluid inlet conduit including a compressible valve section for mounting to the first valve operating means, a fluid outlet conduit, including a compressible valve section for mounting to the second valve operating means, a fluid column connected at a lower end to the fluid inlet and fluid outlet conduits and arranged for mounting to the first and second fluid sensing means and a pump, connected to an upper end of the fluid column tube, and arranged for mounting to the motor for varying air pressure in the column tube.

In accordance with the invention there is provided a motor set for an enteral delivery system which includes first and second compressible valve operating means arranged for receiving compressible fluid inlet and outlet conduits of a delivery set. There is further included first and second vertically spaced fluid column sensing means for detecting the presence of fluid in a fluid column mounted thereon. A pump activating motor is arranged to receive and operate a pump on a delivery set for varying air pressure in the fluid column. Means are provided for controlling the operation of the valve operating means and the motor in responose to fluid detection by the first and second fluid column sensing means.

In accordance with the invention, there is provided a method for pumping fluid from a fluid supply to a fluid outlet in incremental fluid volumes. According to the method there is provided a vertically oriented fluid column and first and second vertically spaced fluid sensors for detecting the presence of fluid in the column. The fluid column is connected to the fluid supply while air pressure in the column is reduced until fluid is detected by the upper fluid sensor. Thereafter the fluid column is connected to the fluid outlet while air pressure is increased in the column until fluid is no longer sensed by the lower fluid sensor, whereby an incremental volume of fluid corresponding to the volume of fluid in the column between the sensors is supplied to the fluid outlet.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
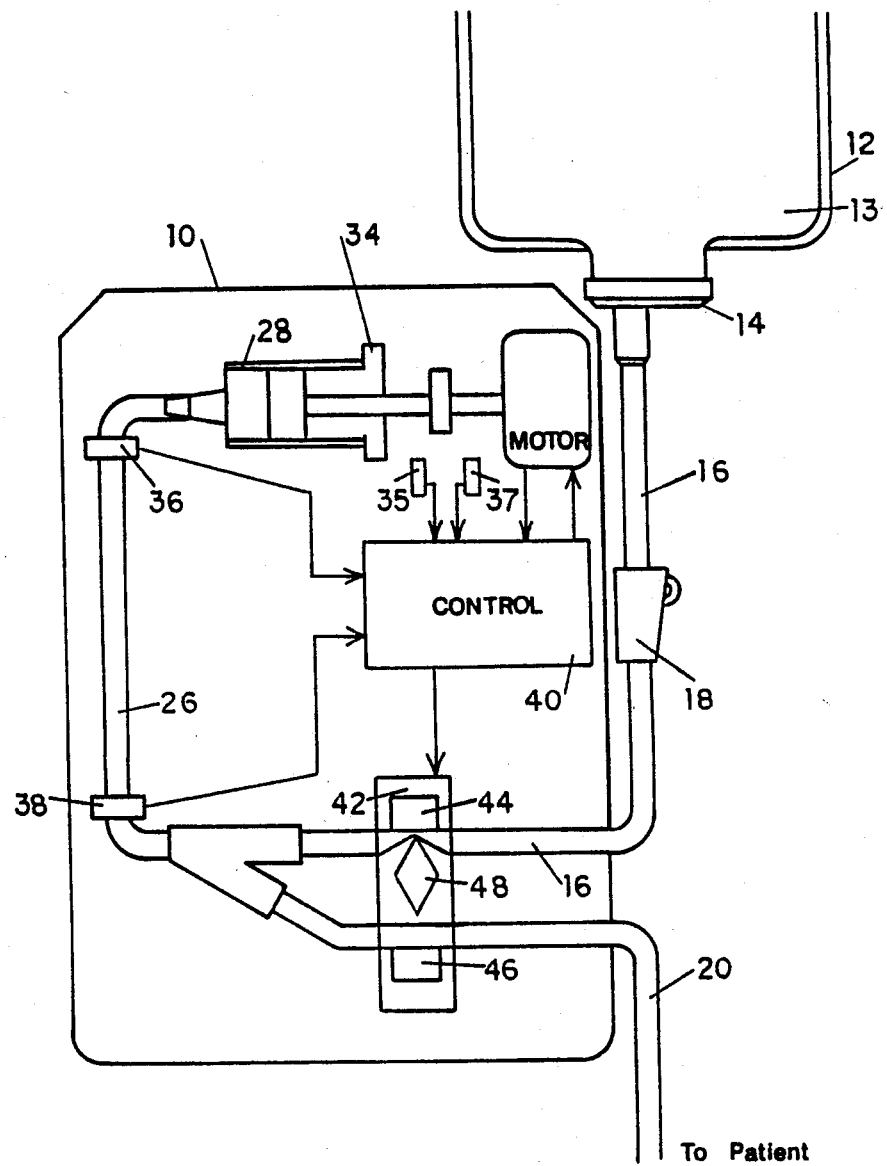
FIG. 1 is an illustration of a fluid delivery system in accordance with the present invention.

Referring to FIG. 1 there is shown an enteral delivery set in accordance with the invention which is mounted to a corresponding motor set for the delivery of fluids, such as enteral nutrition fluids, in carefully measured incremental volumes to a patient. The set illustrated in FIG. 1 includes a fluid supply bag or bottle 12 containing enteral fluid 13. A cap 14 is provided which connects the fluid supply 12 to a fluid inlet tube 16 which also includes a crimp valve 18 of conventional design. Inlet tube 16, passes through an inlet valve mechanism 42 which is arranged to clamp a compressible valve section on tube 16. Thereafter inlet tube 16 is connected to a Y-connector 22 which also connects to fluid column tube 24 and fluid outlet tube 20 by which fluid is delivered to a patient. Fluid outlet tube 20 also includes a compressible valve section which passes through valve mechanism 42. Fluid column tube 24 includes a column section 26 which is connected at its upper end to the barrel 28 of a conventional disposable syringe which includes a syringe piston 30 connected to a reciprocating shaft of motor 32. Syringe barrel 28 is firmly mounted by means 34 to the enteral delivery motor set 10. The motor set 10 further includes an upper fluid sensor 36 and a lower fluid sensor 38 both of which are connected to a control unit 40. Fluid sensors 36 and 38 may be optical fluid sensors which sense the meniscus at the top of a fluid column, or preferably may be ultrasonic fluid sensors, which sense the presence or absence of a fluid in column 26. Valve 42 includes moveable valve operating member 48 which has two positions. In the upper position valve operating member 48 compresses the valve portion of inlet tube 16 against stop 44, thereby closing passage of fluid in inlet tube 16. In the lower valve position valve operating member 48 compresses the valve portion of outlet tube 20 against stop 46 thereby preventing the flow of fluid in outlet tube 20.

Figure 2:
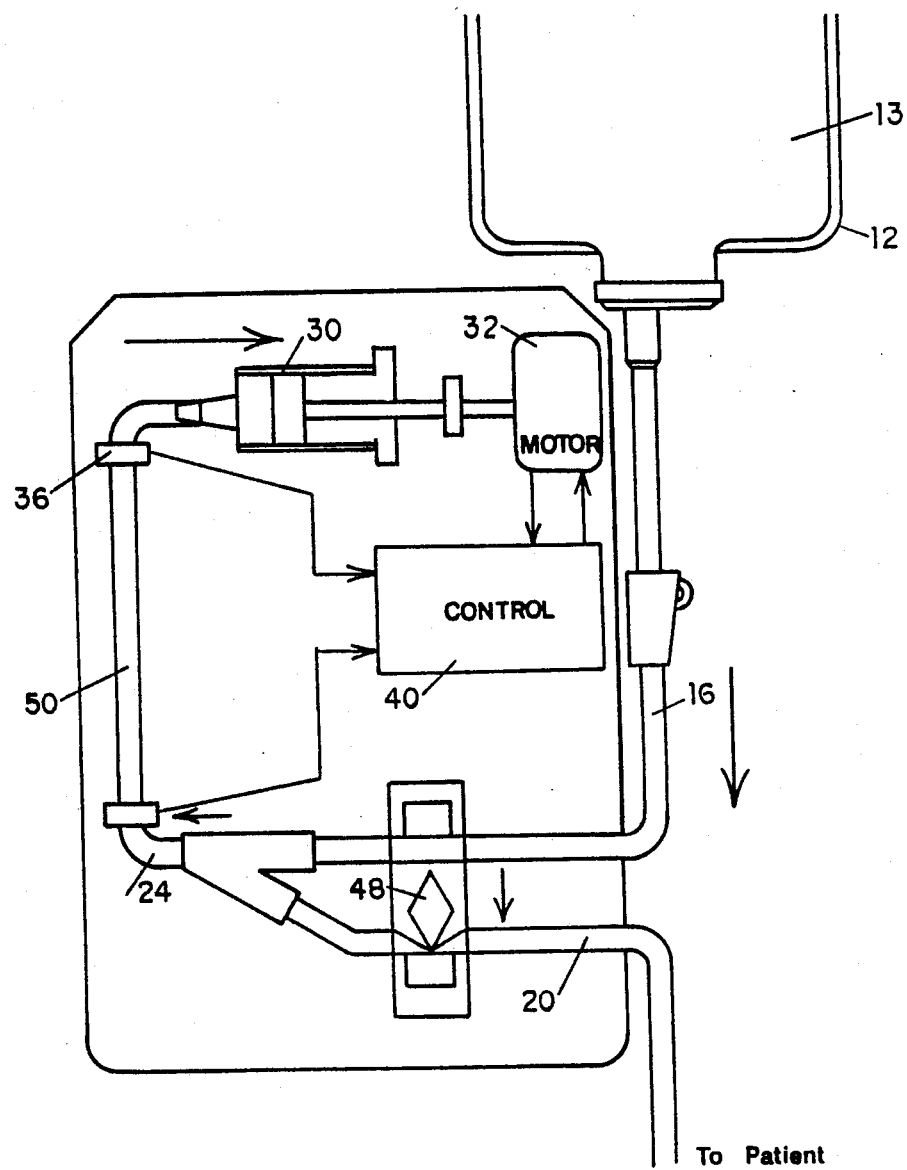
FIGS. 2A, 2B, 2C and 2D are simplified drawings of the fluid delivery system of the present invention which illustrate the sequence of operation.

The operational sequence of the pump and delivery set for delivering incremental volumes of fluid to a patient is illustrated in detail in FIGS. 2A, 2B, 2C and 2D. Referring to FIG. 2A valve member 48 is moved to the lower position to close outlet tube 20, and motor 32 is operated to draw piston 30 to the right thereby reducing the air pressure in fluid column 26 so that the fluid level 50 rises in column 26 until fluid is detected by upper fluid sensor 36. When fluid is detected by sensor 36, a signal is provided to control unit 40 which causes motor 32 to stop moving to the right at the position of FIG. 2B. Thereafter valve member 48 is moved to the upper position closing inlet passage 16 and opening outlet passage 20. Control unit 40 then causes motor 32 to move piston 30 to the left as illustrated in FIG. 2C to increase the air pressure in fluid column 26 and cause the fluid level 50 to descend in column 26 until the absence of fluid is detected by fluid sensor 38. The absence of fluid at fluid sensor 38 causes control unit 40 to stop the left movement of motor 32 at the position of FIG. 2D. The sequence is then repeated. It may be seen that the action of FIGS. 2A through 2D causes a controlled volume of fluid corresponding to the length 54 and inner diameter of fluid column 26 to be provided to outlet tube 20. Accordingly, the stroke 52 of piston 30 must have a volume which corresponds approximately to the volume of fluid in the fluid column which is delivered to outlet tube 20 at each incremental stroke. FIG. 2D illustrates the fluid position at the lower most position when the system is ready to again start the intake of an incremental volume of fluid by the movement of valve 48 to the lower position and movement of motor 32 to the right.

The arrangement of the present invention provides a controlled incremental volume of fluid from the supply 12 to the outlet tube 20 with each stroke of motor 32. The frequency at which such motor strokes will occur and the speed of motion of the motor can naturally be controlled to provide a carefully measured rate of fluid delivery to a patient.

The fluid delivery set of the present invention is relatively inexpensive, since it consists merely of tubing, a single Y connection, and a inexpensive disposable syringe barrel and piston. Further, the set is relatively easy to use as compared to pumping arrangements wherein fluid is directly pumped by a syringe, since it is unnecessary to prime fluid into the syringe itself. During initial operation, fluid can be allowed to flow in a natural manner from the fluid supply 12 through tube 16 to fill tube 20 and tube 24 up to its natural volume determined by the air pressure in the upper portion of tube 26. Operation of the system depends on detection of the top of the fluid column, and therefore accurate priming is not necessary and the elimination of air in the syringe is not necessary. Control unit 40 will cause the operation of motor 32 to adjust to whatever level of fluid results in column 26 by the initial priming operation, since the total volume of syringe 28 is adequate to adjust the fluid level from above or below the normal range between sensors 36 and 38. A further advantage of the invention is that it does not use self-operating valves, which are complex and expensive to include in a fluid delivery set. As noted, the valves of the delivery system of the present invention are provided by operation of active valve member 48 on inlet tube 16 and outlet tube 20 under the control of control unit 40.

In a preferred arrangement of the invention motor set 10 is provided with limit switches 35 and 37 which detect the motion of piston 30 beyond its normal range, as would occur in the event of an abnormal fluid delivery condition. If an occlusion occurs in outlet tube 20 or a subsequent part of the fluid delivery system which prevents the passage of fluid to a patient, piston 30 will move beyond its normal range to the left without causing the fluid level in column 26 to fall below sensor 38. When piston 30 reaches limit switch 35 motor set 10 will cease operation and alert attending personnel to the abnormal condition.

Likewise, in the event the fluid in fluid supply 12 is completely depleted or inlet tube 16 is obstructed, when piston 30 moves to the right, the absence of available fluid will prevent fluid level 50 from rising to sensor 36. Motor 32 will therefor move piston 30 to the right until piston 30 engages limit switch 37, again indicating an abnormal condition, causing control 40 to discontinue operation of motor set 10 and signal attending personnel that the system requires attention.

Figure 3:
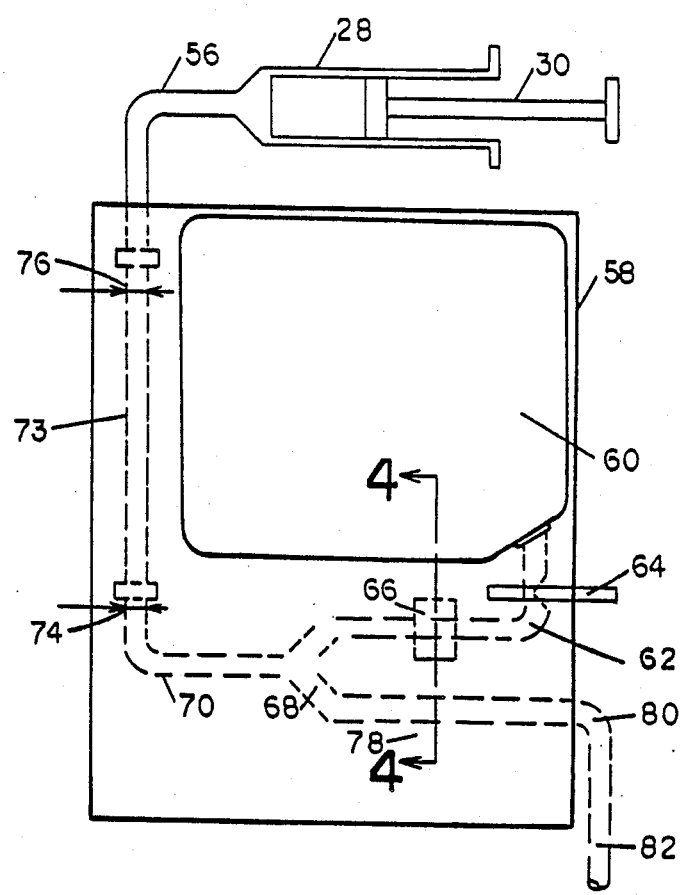
FIG. 3 is an illustration of an alternate embodiment of a fluid delivery set in accordance with the present invention.

FIG. 3 is an illustration of an alternate and possibly less expensive delivery set which utilizes the present invention. The delivery set of FIG. 3 is almost entirely contained within a fluid delivery bag 58 which is formed of two plastic films which are fused together in a particular pattern to form fluid conduits and chambers. In addition to unit 58 there is provided a syringe tube 56, a disposable syringe 28 with piston 30 and an outlet tube 82. A fluid chamber 60 is provided within unit 58 and includes a molded or sealed in place conduit 62 which connects to valve section 66, junction section 68 and connecting conduit 70. Conduit 62 may be closed by slip-on clip 64. Fluid column 72 which includes sensor positions 74 and 76, is integrally formed by the plastic films of unit 58. Alternatively, tube 56 may be longer and connect to conduit 70 to form the fluid column. Inlet valve 66 and outlet valve 78 in outlet conduit 80 are formed by providing an insert between the plastic films and sealing the plastic films around the insert. The insert prevents the plastic films from adhering together as a result of the squeezing of the valve sections during operation.

Figure 4:
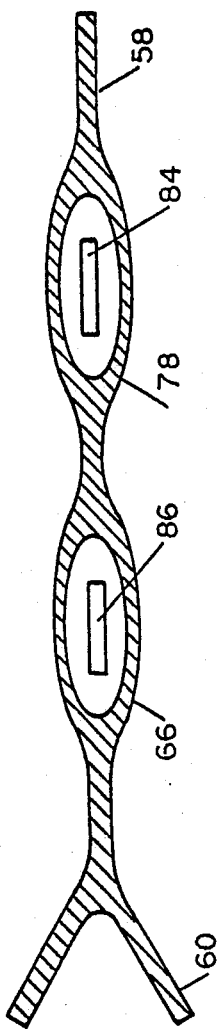
FIG. 4 is a cross-sectional view illustrating the valve portions of the delivery set of FIG. 3.
Figure 5:
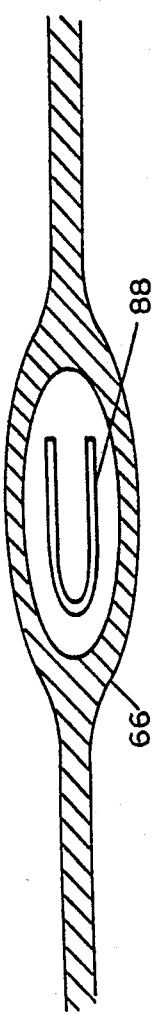
FIG. 5 is a cross-sectional view of an alternate valve arrangement for the delivery set illustrated in FIG. 3.

FIG. 4 is a cross-sectional view which shows in detail the arrangements for valves 66 and 78. Upper and lower films which are used to form reservoir 60 are fused together on both sides of the valves 66 and 78, forming a conduit. Between the film members inserts 84 and 86 are provided, which may be small pieces of material which does not adhere to the thermoplastic films forming unit 58. Inserts 84, 86 may typically be small pieces of teflon or the like. Inserts 84, 86 prevent the upper and lower films of the valve members from adhering to each other during repeated valve operations. FIG. 5 shows an alternate arrangement for valve member 66 wherein the insert is a plastic material which has a C-shaped cross section to provide a spring action to cause the valve to open more easily. Another alternate is an insert with an S-shaped cross-section.

Figure 6:
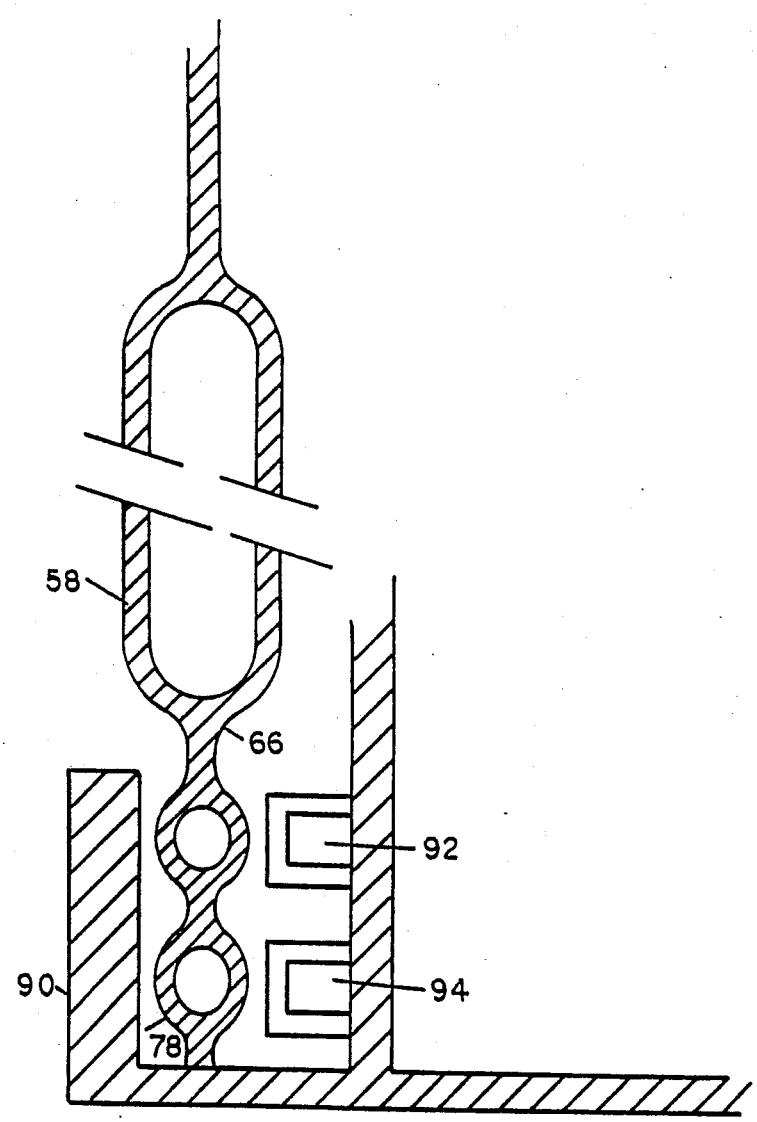
FIG. 6 is a cross-sectional view of the mounting of the delivery set of FIG. 3 to a pump motor set.

FIG. 6 is a cross-sectional view of the engagement of valves 66 and 78 to valve operating members 92 and 94 on a pump. A pump housing extension 90 is provided into which the valve portion of unit 58 is inserted. When valve operating members 92 and 94 are extended from the main portion of the pump housing they compress valves 66 and 78 respectively to provide the required opening and closing operation.

While there have been described what are believed to be the preferred embodiments of the present invention, those skilled in the art will recognize that other and further modifications may be made thereto without departing from the spirit of the invention, and it is intended to claim all such changes and modifications as fall within the true scope of the invention.

We claim:

1. A delivery set for a medical fluid delivery system comprising an inlet fluid conduit for connection to a supply of fluid, a first compressible valve section in said inlet fluid conduit, an outlet fluid conduit, a second compressible valve section in said outlet fluid conduit, a fluid column having a selected length and cross-section corresponding to an incremental fluid volume and connected at its lower end to said fluid inlet and outlet conduits, and means for varying air pressure in said fluid column, said means being connected to said fluid column, wherein said fluid supply and said fluid conduits are formed between plastic films.

2. A delivery set as specified in claim 1 wherein said fluid column is formed between said films.

3. A delivery set as described in claim 2 wherein said means for varying air pressure comprises a syringe.

4. A delivery set as specified in claim 1 wherein said first and second compressible valve sections include valve inserts between said films forming said conduits.

5. A delivery set as specified in claim 4 wherein said valve inserts have a C-shaped cross-section.

6. A delivery set as described in claim 5 wherein said means for varying air pressure comprises a syringe.

7. A delivery set as described in claim 4 wherein said means for varying air pressure comprises a syringe.

8. A delivery set as described in claim 1 wherein said means for varying air pressure comprises a syringe.

9. A medical fluid delivery system comprising a motor unit and a disposable delivery set, said motor unit comprising:
   first and second compressible valve operating means;
   a first and second valve;
   first and second vertically spaced fluid sensing means;
   a reciprocating pump activating motor; and
   means for controlling operation of said valve operating means and said pump activating motor to open said first valve, close said second valve and operate said motor in a first direction until fluid is detected by said first sensing means and to close said first valve and open said second valve and operate said motor in a second direction until fluid is no longer detected by said second sensing means;
   said disposable delivery set comprising:
   a fluid inlet conduit, including a compressible valve section for mounting to said first valve operating means;
   a fluid outlet conduit, including a compressible valve section for mounting to said second valve operating means;
   a fluid column connected at a lower end to said fluid inlet and fluid outlet conduits and arranged for mounting to said first and second fluid sensing means;
   wherein said conduits and said fluid column are formed between plastic films;
   and a pump connected to an upper end of said fluid column and arranged for mounting to said pump activating motor for varying air pressure in said column.

10. A medical fluid delivery system as specified in claim 9 wherein said first and second valve operating means comprises a unitary valve operating member moveable between two positions for closing said first valve and opening said second valve in a first position and for opening said first valve and closing said second valve in a second position.

11. A combination of a motor unit and a delivery set for a medical fluid delivery system comprising first and second compressible valve operating means arranged for receiving compressible fluid inlet and outlet conduits of a delivery set, first and second vertically spaced fluid column sensing means for detecting the presence of fluid in a fluid column between the inlet and outlet conduits mounted thereon, a pump activating motor arranged to receive and operate a pump on a delivery set for varying air pressure in the fluid column, and means for controlling operation of said valve operating means and said pump activating motor in response to fluid detection by said first and second fluid column sensing means, with said conduits and said fluid column for said motor unit being formed between plastic films.

12. A motor unit specified in claim 11 wherein said first and second valve operating means comprises a unitary valve operating member moveable between two positions for closing said first valve and opening said second valve in a first position and for opening said first valve and closing said second valve in a second position.

13. A motor unit as specified in claim 11 wherein said fluid column sensing means comprises optical sensing means.

14. A motor unit as specified in claim 11 wherein said fluid column sensing means comprises ultrasonic sensing means.

15. A motor unit as specified in claim 11 wherein said motor has a reciprocating member and wherein there are provided means for detecting excess movement of said reciprocating member.

16. A method for pumping a medical fluid from a fluid supply to a fluid outlet in incremental fluid volumes, comprising:
 providing a vertically oriented fluid column and first and second vertically spaced fluid sensors for detecting the presence of fluid in said column;
 connecting the lower end of said fluid column to said fluid supply and reducing air pressure in said column until fluid is detected by the upper fluid sensor;
 and connecting the lower end of said fluid column to said fluid outlet and increasing air pressure in said column until fluid is no longer sensed by said lower fluid sensor whereby an incremental volume of fluid corresponding to the volume of fluid in said column between said sensors is supplied to said fluid outlet,
 wherein said fluid supply and said fluid column are formed between plastic films.

* * * * *